(12) United States Patent
Weber et al.

(10) Patent No.: US 6,764,493 B1
(45) Date of Patent: *Jul. 20, 2004

(54) TISSUE REMOVAL USING BIOCOMPATIBLE MATERIALS

(75) Inventors: Paul J. Weber, Ft. Lauderdale, FL (US); Luiz B. Da Silva, Danville, CA (US); Alexander M. Rubenchik, Livermore, CA (US)

(73) Assignee: Pearl Technology Holdings, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/710,478

(22) Filed: Nov. 10, 2000

Related U.S. Application Data (63) Continuation-in-part of application No. 09/234,224, filed on Jan. 20, 1999, now Pat. No. 6,306,119.

(51) Int. Cl.[7] .............................................. A61B 17/50
(52) U.S. Cl. ......................... 606/131; 606/20; 604/291; 451/75
(58) Field of Search ................... 606/131, 20; 604/290, 604/291; 451/39, 75

(56) References Cited

U.S. PATENT DOCUMENTS

| | | | | |
|---|---|---|---|---|
| 4,703,590 A | * | 11/1987 | Westergaard | |
| 5,616,067 A | * | 4/1997 | Goenka | 451/39 |
| 5,620,414 A | | 4/1997 | Campbell, Jr. | 604/22 |
| 5,779,523 A | * | 7/1998 | Mesher | 451/93 |
| 5,820,447 A | * | 10/1998 | Niechcial | 451/99 |
| 5,910,042 A | * | 6/1999 | Niechcial | 451/39 |
| 5,913,711 A | * | 6/1999 | Visaisouk | 451/39 |
| 5,961,732 A | * | 10/1999 | Patrin et al. | 134/7 |
| 5,971,999 A | * | 10/1999 | Naldoni | 606/131 |
| 6,080,165 A | * | 6/2000 | DeJacma | 606/131 |
| 6,174,225 B1 | * | 1/2001 | Becker | 451/75 |
| 6,226,996 B1 | * | 5/2001 | Weber et al. | 62/126 |
| 6,264,666 B1 | * | 7/2001 | Coleman et al. | 606/131 |
| 6,306,119 B1 | * | 10/2001 | Weber et al. | 604/290 |

FOREIGN PATENT DOCUMENTS

| | | | |
|---|---|---|---|
| EP | 0 324 448 A1 | * | 7/1989 |
| EP | 0 564 392 A2 | * | 10/1993 |
| GB | 2095538 A | * | 10/1982 |
| WO | WO 97/11650 | * | 4/1997 |
| WO | WO 99/20336 | | 4/1999 |
| WO | WO 99/37229 | | 7/1999 |

* cited by examiner

*Primary Examiner*—Ralph A. Lewis
(74) *Attorney, Agent, or Firm*—John P. Wooldridge (57) ABSTRACT

Biocompatible materials are propelled at the skin with sufficient velocity to cause desired resurfacing of tissue to the desired penetration depth. The materials, such as dry ice or water ice, are harmonious with the human body and thus eliminate foreign body reactions. Various materials may be used in combination, including local anesthetics and vasoconstrictors in solid or liquid form. The biocompatible solid or liquid particles are suspended in a cold carrier fluid and propelled through an insulated delivery system to the surface of the skin. The treatment of diseased skin lesions may be accomplished using the present invention as a drug delivery system.

54 Claims, 5 Drawing Sheets

TISSUE REMOVAL USING BIOCOMPATIBLE MATERIALS

This is a continuation in part of U.S. patent application Ser. No. 09/234,224, titled "Skin Resurfacing and Treatment Using Biocompatible Materials", filed Jan. 20, 1999 now U.S. Pat. No. 6,306,119.

BACKGROUND OF THE INVENTION

1. Field of the Invention

The present invention relates to techniques for cleaning, resurfacing or treating human tissue (e.g., skin) using biocompatible materials propelled into the surface of the tissue.

2. Description of Related Art

Resurfacing the human skin can be achieved by several mechanisms that are aimed primarily at disrupting the epidermal and upper dermal layers. Human skin is composed of at least three layers of variable thickness, depending upon body location. The uppermost layer, or epidermis, is usually as thin as a sheet of paper. The layer just below the epidermis is the dermis, which is largely composed of collagen and makes up the "leather" layer of the skin. The dermis may vary in thickness from that of paper (50–100 $\mu$m) to as thick as half an inch on the neck and back. The layer below the dermis may be composed of either muscle (around the eyes and mouth) or fat, otherwise known as subcutaneous fat.

New human surface skin is regenerated following resurfacing by the surrounding islands of normal epidermis and epidermal cells migrating from the deep hair pores and other pore structures that permeate the upper dermis, mid dermis, and epidermis. If excessive scar tissue, rather than a plethora of epidermal cells, closes a surface wound, then an unsightly scar will result The key to all resurfacing procedures is a controlled destruction of the desired area that still allows the regeneration of new tissues from pores and neighboring islands of untouched, untreated skin.

The procedures currently used in human skin resurfacing include chemical peeling, dermabrasion, laser surgery, and most recently the "power peel" or crystalline peel. In chemical peeling, a caustic, disruptive or destructive liquid agent is applied to the surface skin to damage existing epidermal and dermal cells, which will then be replaced by the body. Peeling agents act depending on their strength and type. Examples of chemical peeling agents include fruit acid peel, glycolic acid peel, and trichloracetic acid (TCA) and phenol peels. TCA peels can be made to act at deeper and varying depths by varying the concentration of TCA used to destroy the surface skin. Concentrations as low as 5–10% TCA will behave similarly to a fruit acid peel, and concentrations of 50% TCA may cause severe peeling burns, which simulates phenol, and may border on scarring. Phenol, when diluted with water, penetrates more deeply and destroys more tissue than most other peeling agents.

Dermabrasion literally means abrasion of the skin and is a procedure in which a rotating sanding wheel, or abrasive substance, is applied to a rigidified skin to sand out an undesirable feature, mark, or scar. Some high-speed dermabrasion rotors go up to 200,000 revolutions per minute (rpm) and do not require any rigidity to the tissues; however, they require extremely skilled personnel and special instrumentation and are impractical for most office use. A minor mistake with such a high-powered machine can have disastrous results. Dermabrasion is usually performed with a rotating wheel operating at speeds under 10,000 rpm after the skin has been rigidified using freon or dichlorotetrafluoroethane. In dermabrasion (unlike laser surgery), the person operating the abrading wheel has a direct tactile sense of pressing the wheel into the tissues being treated and can apply differential pressure to areas of elevation. Dermabrasion can be achieved to various depths depending upon the depth of freezing (rigidification), the number of passes of the abrader, the type of abrasive wheel, and the pressure applied. This procedure is waning in use, however, due to the unavailability of freon.

Laser surgery has recently become popular to remove or reduce wrinkles, remove tumors, and alter scars, although results are mixed. Several types of lasers are used, including carbon dioxide and erbium-YAG lasers. Carbon dioxide lasers deliver light radiation at 10 $\mu$m, which can vaporize and destroy surface skin. These lasers may be set on various pulse patterns to deliver precise and controlled amounts of laser radiation to the skin in a relatively uniform and homogenous fashion across the surface. An unfortunate disadvantage of this laser is that heat can be transmitted to the surrounding tissues. Additionally, after the first pass of the carbon dioxide laser, the skin begins to ooze and become wet at the surface as fluids build up in response to the damage. Since water and blood absorb in the infrared region, a second pass of the laser will penetrate to a variable depth, depending on how much surface ooze there is in the area. The ooze prevents the laser energy from reaching the target tissues uniformly. During laser irradiation, the tissues may begin to desiccate, which ultimately results in severe thermal damage. Depositing too much laser energy on the target tissues can result in persistent redness, scarring, and other complications or damage, even with thermal relaxation techniques to mitigate heat transfer.

Although other lasers, such as the erbium-YAG laser or combination $CO_2$/erbium laser, were developed in an attempt to reduce bleeding and thermal damage, serious scarring and persistent redness can still result If the penetration depth of the damage is complete and the regenerating skin structures are destroyed, scarring will ensue. Scarring is the unwanted presence of large amounts of collagen in the upper surface, with a minimal amount of normal appearing epidermis to lend a normal appearance to the skin. When scars are treated with certain lasers, the light does not actually remove or destroy collagen, but usually affects the hemoglobin and other blood pigments. The reduction of blood vessels to the scar causes an optical effect that makes the scar less noticeable.

Microdermabrasion (MDA) also known as "The Power Peel" is a relatively new treatment patented by Molinari in U.S. Pat. No. 5,037,432. MDA has been used in Europe for the last decade. MDA is a process by which aluminum oxide crystals, which are extremely rigid, strong, rasping and irregular-shaped, are projected onto the skin by air that is driven by pressures neighboring 25 pounds per square inch. Safe operation of these devices requires the use of a limited number of passes or a minimal pass speed over the target area. Most power peels are designed to remove the epidermis of the skin. However, epidermal removal will not result in any alteration of scar formation. Almost all "foreign" objects are unwanted by the body. This also includes particles that are apparently inert such as sand. There are a few problems with aluminum oxide crystals and their use on the face as a peeling agent. If proper depth were attained in order to remove, destroy or alter deeper structures such as scars, pores or pits; then granuloma formation would result from the impact and placement of the aluminum oxide into the structures of the skin and the surrounding skin tissue. This is not wanted and leads to unsightly scarring. There are three main systems, of MDA used in America today; some of the systems come with a vacuum apparatus to partially suck away unwanted particles. The MDA vacuum apparatus sucks most but not all of the crystals passed. Since aluminum oxide crystals can cause foreign body reactions, even a small amount of them could be unwanted or lead to cellular difficulties later on in life. Therefore, since a MDA machine vacuum cannot be made 100 percent efficient, the power peel should not be used at a depth below the epidermis. Two potentially serious problems have now been proposed regarding MDA. Silicosis or coal miners' lung disease is frequently fatal; sand-like particles are spun into the air (of coal mines) coating the lungs with material that causes delayed foreign body reactions years later and interferes with breathing. In MDA the ultra-fine particles are like miniature sandspurs and are easily inhaled by the patient, thus causing a potential lung disease years from the time of exposure. Additionally, the aluminum oxide particles can deposit on the conjunctiva of the eye latching on and never letting go and causing conjunctivitis (pink eye) that may be permanent.

A relatively new twist on MDA is to have a separate canister of crystallized vitamins able to be tapped and in the gas flow loop of the aluminum oxide crystals to provide the mechanical "peeling" and some claimed effect of skin vitamin replenishment. Problems have arisen because any humidity in the system causes the powderized vitamins to crystallize or clump, thus clogging the microdermabrasion delivery device. The vitamin or attendant particles also do not impact on the same exact cellular location that the abrasive impacts in this type of delivery system.

WO-9937229 by Coleman et al. disclose propelling water at high speeds and pressures to cut or alter tissues. The use of water as the carrier vehicle has several major drawbacks and disadvantages. As in the time-honored process of dermabrasion (described above), freezing the skin rigid allows controlled application of energy to reduce defects. In order to immobilize skin for uniform abrasion (so that it does not deform or invaginate at treatment) temperatures well below 0 degrees Centigrade are required. Water, even when mixed with large quantities of ice cannot achieve the desired skin-immobilizing temperatures well below 0 degrees (even when not at standard pressure). Additionally, the patent by Coleman et al. would not be effective in delivering chemicals to the skin that could not be miscible with water or in solution with water unless a constant stirring mechanism was included in all portions of the Coleman system; liposomes and oil-soluble materials would separate and likely segregate into a non-uniform spray in the liquid-water-driven Coleman patent The Coleman system would likely not uniformly expose the dermal layers so that effective application of vitamins and other medicaments could be delivered to even the upper-mid dermal layers of the skin.

Current treatments for skin at risk for infection due to thermal burns, chemical burns or other trauma or disease include removal by "cold steel" otherwise known as scalpel/scissor debridment and more recently by laser. By and large, debridment procedures may be painful if the nerves supplying the living tissues adjacent to the compromised tissue are still functional. This is because for the surgeon to be sure of having removed the devitalized tissues most debridment procedures are performed until bleeding is noticed (a property that is usually indicative that living/good tissue has been reached) thus ensuring that all the dead tissue has been removed. Again, dead tissue is a culture dish, lacking any antibiotics or other medicines that could halt the spread and feeding of infectious organisms.

Tissues that may need to be debrided include the largest organ (skin) following burns from fire, chemicals, blasts, etc. Also included are any exposed and damaged internal components, mostly comprising the muscle and fatty tissues just underlying the skin following blast or kinetic energy trauma. Further included may be open organs from the abdominal cavity following blast injuries, even including the bowel.

The deep but fine firing of biocompatible or bioabsorbable compounds or drugs in an aqueous vehicle, especially antibiotics (antibacterial, antiviral, anti-fungal) onto the human skin, may allow deep treatment of damaged, or devitalized skin and tissue. The device may perform the optimal multiple functions of not only removing unwanted tissues but leaving behind desirable chemicals/medicines in order to improve the remaining tissues or prevent the growth of unwanted organisms or undesirable tissue reactions.

Thus, it would be advantageous to develop a procedure for removal of scars, wrinkles, and various other imperfections or lesions on the skin, as well as debridment of burns and cleaning of wounds, without introducing foreign bodies or substances that cause adverse physiological reactions or produce thermal damage. The present invention provides such advantages by using materials that are biocompatible.

SUMMARY OF THE INVENTION

The present invention is a method and apparatus for resurfacing or treating tissue using biocompatible, non-toxic materials that are propelled at the tissue with sufficient velocity to cause destruction or loosening of tissues to the desired depth upon impact This is a continuation in part of U.S. Pat. No. 6,306,119. "Skin Resurfacing and Treatment Using Biocompatible Materials", filed Jan. 20, 1999 and incorporated herein by reference. One objective of the invention is to blast materials into the tissue that are harmonious with the human body and thus do not cause foreign body reactions, which lead to granulomas and scarring. The materials must be hard enough (crystalline) or propelled at high enough velocities to remove tissue. Suitable resurfacing materials include solid carbon dioxide (dry ice), ice (frozen $H_2O$), organic materials such as urea, or other amines (including amino acids) or amides, organic polymers such as sugars, carbohydrates, or proteins, and inorganic salts such as phosphates, sulfates, carbonates and nitrates. To relieve. pain, a local anesthetic may be used separately or in combination with the biocompatible materials used to resurface the skin. Antibiotics could be included to prevent infection; bioabsorbable or biodegradable compounds or drugs can be delivered to the skin to treat diseases. Vasoconstrictors, such as adrenaline, can be placed into crystalline form and fired into the skin to constrict blood vessels on the surface of the skin to prevent bleeding. In addition vitamins including fat soluble (A, D, E, K) and water soluble vitamins (B complex, C), as well as co-enzymes, antioxidants, minerals, depigmenting medicines, antibiotics and other medicaments can be incorporated into the. biocompatible materials.

In the present invention the biocompatible materials are suspended in a carrier fluid (e.g., a cold gas) and propelled through a delivery tip or nozzle to the surface of the skin or tissue to be treated. Suitable carrier fluids include dry air or gaseous nitrogen, helium, argon, or gaseous $CO_2$. An optional vacuum system used in conjunction with the delivery system can be used to remove excess materials or reaction by-products that build up on the surface of the skin. The biocompatible crystals or droplets are maintained at the proper temperature (e.g., freezing) in the delivery system. Initially, the biocompatible materials may be contained in a frozen solid block, and particles of the appropriate size are generated using various means, including grinding or sonication. Alternatively, resurfacing particles are formed by spraying microdroplets of the desired substance or mixture via jets or atomizing nozzles into a cold carrier fluid, which freezes or cools the droplets (aerosol).

In one embodiment the treatment system consists of a control unit, a carrier fluid delivery system and handheld particle generator. The control unit can include user controls to select carrier fluid temperature, initial pressure and vacuum. The delivery system consists of an insulated tube and electronic wires that power motors in the handheld device. The handheld particle generator, contains a mechanism to push a frozen block of biocompatible material against a rotating grinding wheel that produces small (<500 micron diameter) particles. The carrier fluid flows through the handheld device, collects the generated particles and then drives then through an exit aperture onto the target tissue. The particle density can be adjusted by controlling the speed of the grinding wheel. The user moves the handheld device over the surface to be treated. By adjusting the particle density and temperature a variety of effects can be achieved. The depth of freezing can also be controlled by the carrier fluid temperature and by adjusting the speed that the device is moved over tissue. The temperature and flow of the carrier gas and biocompatible particles are monitored with sensors in the control unit and- optionally at the handheld device. The carrier fluid temperature is maintained at least at temperatures low enough to prevent particle melting. Optional infrared temperature sensors attached to the handheld device can be used to monitor surface temperature and guide the user through the treatment. Other possible sensors include pressure at the exit aperture, carrier fluid and particle velocity. An accurate measurement of the particle velocity and particle size can be used to estimate the penetration depth.

An objective of the present invention is to provide a method and apparatus to remove scars, wrinkles, and other imperfections of the skin (or other tissue) without introducing foreign bodies or substances that cause adverse physiological reactions or produce thermal damage. Another objective of the present invention is to provide a method and apparatus to clean wounds and perform burn debridment Another objective of the invention is to provide a delivery system for delivering or depositing drugs or other medicaments at the desired depth in the epidermis or dermis for treatment of diseased skin lesions, e.g., pre-cancers. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

FIG. 1 shows one embodiment of the present invention where the control unit is connected to the handheld device by a delivery tube and cable.

FIG. 2 shows a detailed cross-sectional view of one embodiment of the handheld device of the present invention.

FIG. 3 shows a block diagram of the key components of the control unit.

FIG. 4 shows an alternative technique for producing the particles where an atomizing nozzle sprays water mist or droplets at a nonperforated sheet, strip or plane contained within a cool container to cause ice crystals to form.

FIG. 5 shows an alternative technique for producing the particles where a vessel is filled with cold carrier fluid through a port.

DETAILED DESCRIPTION OF THE INVENTION

The present invention is a method and apparatus for resurfacing or treating tissue (e.g., skin) using biocompatible materials that are blasted/propelled at the tissue with sufficient velocity to cause destruction, loosening, or unbinding of tissues to the desired depth upon impact The penetration depth of the particles is controlled by the operator. The materials that are propelled into the skin are non-toxic and harmonious with the human body and thus do not cause foreign body reactions (which may lead to granulomatous disease and/or scarring). The materials must be hard enough (crystalline) or propelled forcefully enough to penetrate to the appropriate depth in the dermis to alter or remove unwanted skin features or tissue. Suitable materials include solid carbon dioxide (dry ice), ice (frozen $H_2O$), organic materials such as urea, or other amines (including amino acids) or amides, organic polymers such as sugars, carbohydrates, or proteins, and inorganic salts such as phosphates, sulfates, carbonates and nitrates. These materials can be used separately or in combination. Many other materials usable in the present invention are described below.

Several considerations are taken into account in the choice of skin resurfacing materials. Biocompatible materials are defined for purposes of this description as materials that can be propelled into the epidermal or dermal layers of the skin without a significant adverse biological (e.g., toxic, inflammatory, carcinogenic, or immunogenic) host response (e.g., foreign body reaction, autoimmune disease, necrosis, apoptosis) be it delayed or immediate. The principle propelled materials should be maintained in a solid (crystalline) form for maximal abrasive capability. The materials are preferably at low temperatures (e.g., <0° C.), although too cold of a material can result in unacceptable tissue death. Human tissues can safely tolerate freezing with ice to a certain extent, for a limited amount of time, before frostbite occurs.

Other biocompatible materials or additives that have an additional function to impart to the skin can be used in combination with the resurfacing materials. Under some circumstances it may be desired that these materials and additives can also be imparted to the skin without the principle propelled resurfacing materials. These additives may be particularly useful in cases where deeper tissue alteration is needed. For example, once the epidermis is penetrated by any surface destructive procedure, pain will result when the dermal nerves are stimulated. To relieve this pain, crystalline local anesthetic such as xylocaine (lidocaine) or any number of topical or local anesthetics could be used, either separately or in combination with other materials. These local anesthetics will dissolve and be carried to the dermal nerves upon impacting the skin. Additionally, vasoconstrictors or blood vessel closing agents such as adrenaline could be fired accompanying the carrier particles into the skin to constrict blood vessels on the surface of the skin to prevent bleeding, which is a common problem with many forms of skin resurfacing (e.g., dermabrasion, laser treatment). Less bleeding is especially desirable and needed if the resurfacing procedure is performed in the deeper skin levels. Buffering agents or hydrophilic materials to absorb surface fluids could also be useful, and antibiotics could be added to prevent infection.

The present invention may be used as a drug delivery system that provides bioabsorbable or biodegradable compounds or drugs by propelling them into the surface of the skin. Biodegradable polymeric systems can be used for drug delivery and offer greater flexibility in the design of delivery systems for large molecular weight drugs, such as peptides and proteins including vaccines. DNA and RNA may also be delivered. Biocompatible gels, like hydrogels, can be grafted onto other biomaterials with good mechanical properties for skin resurfacing. The combination can accomplish both skin resurfacing and drug delivery in the epidermis and dermis. Water insoluble polymers such as poly (glycolic acid) have been investigated as biodegradable drug delivery systems.

For dermatological applications, the present invention may be used to deliver drugs for treatment of precancerous or cancerous lesions in the epidermis and dermis. The topical delivery of certain medicines often cannot penetrate deeply or uniformly enough, and long-term topical application of the creams or gels is inconvenient for the patient To achieve long-lasting, deeper skin treatment for lesions, drugs (e.g., 5-fluorouracil) in a crystal or gel form may be propelled with a carrier particle into the skin to penetrate the deep epidermis.

Figure 1:
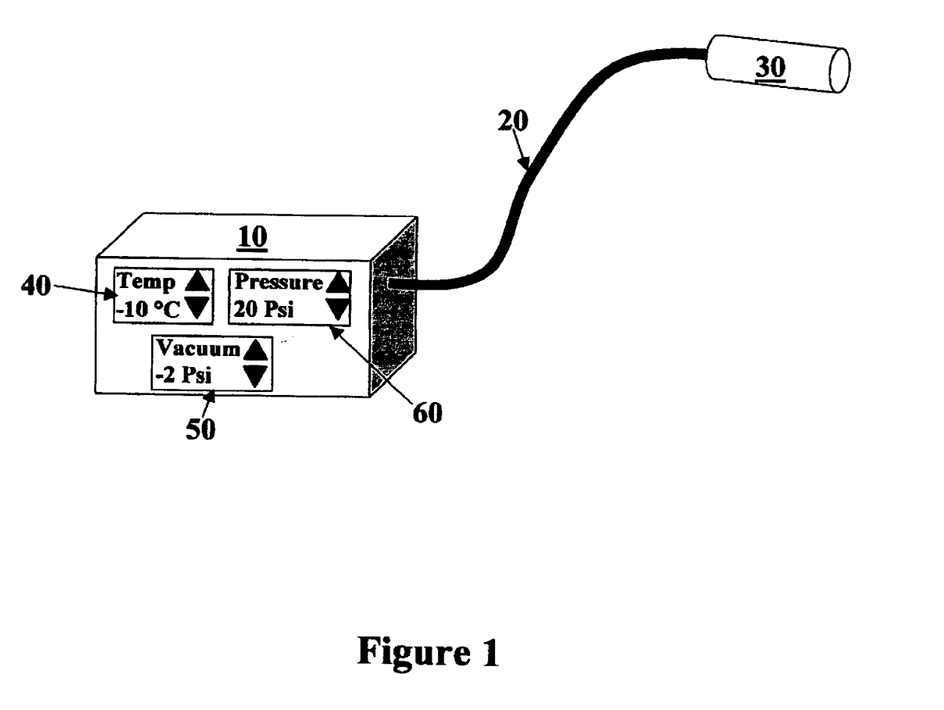

FIG. 1 shows one embodiment of the present invention where the control unit 10 is connected to the handheld device 30 by a delivery tube and cable 20. The control unit 10 contains an air compressor and cooler that produce a carrier fluid that goes through a tube contained within the tube/cable assembly 20. The carrier fluid can be dehumidified air or any inert gas such as nitrogen, helium, or argon. The desired carrier gas temperature and pressure is controlled by adjusting the settings 40, 50 respectively on the control unit 10. The pressure of the carrier fluid in the delivery system is typically about 25 psi but may be controllably varied. The delivery tube 20 may be optionally accompanied by a vacuum tube that removes excess materials or reaction by-products that build up on the surface of the skin. The vacuum pressure can be controlled by adjusting the settings 60 on the control unit 10. Electronic cables contained within the tube/cable assembly 20 carry power to the handheld device and return optional signals from sensors within the handheld device. The delivery tube 20 and handheld device 30 can be insulated to maintain the carrier fluid and biocompatible crystals or droplets at the proper temperature (e.g., freezing). In normal use the handheld device 30 is scanned over the tissue to be treated.

Figure 2:
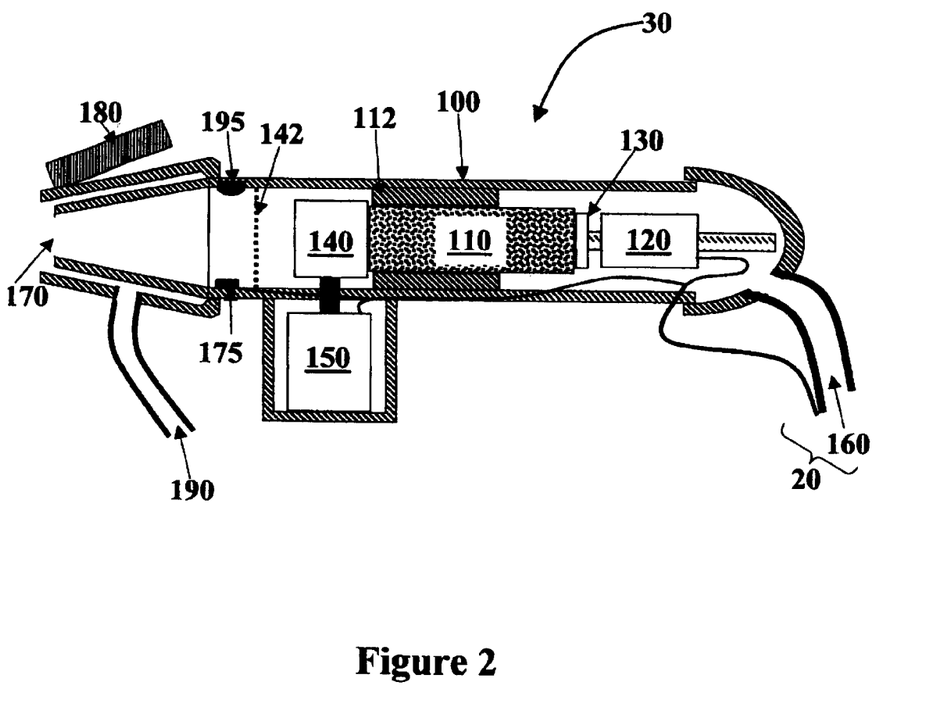

FIG. 2 shows a detailed cross-sectional view of one embodiment of the handheld device 30. The handheld device consists of a housing 100 that is insulated to protect the user. An optional electric heater could be integrated into the outside wall of the device 30 to improve user comfort A specially shaped frozen block of the biocompatible material (e.g. ice) 110 is located within the device 30. Biocompatible material 110 is held in place by packing material 112. An electric motor 120 drives a piston 130 that pushes the block 110 onto a rotating grinder wheel 140 that is driven by a second electric motor 150. The electric motors are powered and controlled through electrical wires that come from the control unit through the delivery tube/cable 20. The speed of the motors can be adjusted to control the particle density. The motors could also be powered pneumatically. As the rotating grinder wheel 140 rotates, biocompatible particles (e.g., ice) are produced which are picked up by the cold carrier fluid that enters the device 30 through the tube 160.

Packing material 112 includes at least one opening that allows the cold carrier gas to flow from tube 160 to the exit aperture 170. The particles exit device 30 through the exit aperture 170. The exit aperture 170 can be a variety of shapes including a narrow slit, rectangle, square, circle, or ellipse. An optional vacuum line 190 is used to pull debris, ice particles or water away from the surface. In order to maximize debris collection, the device 30 could be placed in contact with the surface to be treated. In this case the carrier fluid would flow down the center of the device 30 and then return through the vacuum tube along with debris and particles. The final segment of device 30 can be made of clear plastic so that the user can easily see the surface and monitor progress.

A variety of possible designs can be used for the grinder wheel 140. In one embodiment the grinder wheel is made of surgical steel and has barbs on the surface to scrape off particles. An alternative design is a grinder wheel that consists of surgical steel wires that form a wire brush. Yet another grinder wheel design incorporates sharp cutting edges into the wheel that scrapes the solid block 110. An optional wire mesh 142 can be placed after the grinder wheel to prevent large particles from exiting the device and striking tissue. An optional temperature sensor 175 near the tip can be used by the control unit 10 to better control the exit carrier fluid temperature. By adjusting the exit carrier fluid temperature it is possible to modify the propelled-particle's shape. Specifically, warmer carrier fluid could be used to melt sharp edges on the particles to provide a smoother and more gentle treatment. Also, an optional infrared temperature sensor 180 can be incorporated into the device 30 to provide the user with the surface temperature of the area being treated. The measured surface temperature can be used by the user to prevent excessive cooling. Alternatively, the infrared temperature sensor 180 reading can be transmitted to the control unit and used to automatically turn off flow if the surface temperature drops below a preset limit An optional light source (e.g., LED) 195 can be used to send a beam of light to illuminate the particles as they move through the final stage. The light scattered by the particles can be seen by the user and provides confirmation that particles are flowing. In addition, an optional light detector filtered for the specific color of light used to illuminate the particles can be used to estimate particle density. In one embodiment the light detector would be positioned perpendicular to the light beam to minimize the collected light when no scattering particles were present. The control unit 10 could record the background detector signal just before starting particle generation. By subtracting this signal from that measured when particles are being generated an estimate of particle density could be calculated and display on the control unit 10.

Figure 3:
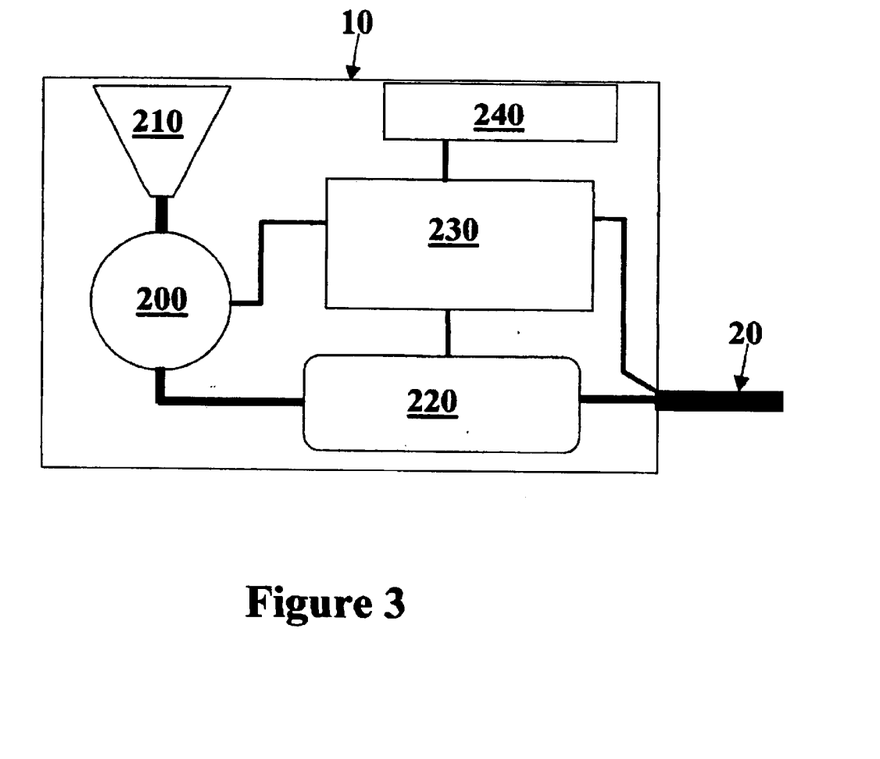

The specially shaped block of biocompatible material 110 is prepared in a special mold by filling the mold with a mixture of water and any desired additives and then putting the mold in a freezer or liquid nitrogen dewar. By using sterile mixtures and molds, the risk of infection can be reduced. FIG. 3 shows a block diagram of the key components of the control unit 10. The control unit 10 contains a compressor 200 that draws room air or bottled air through a filter/dehumidifier 210. The pressurized air is then transported through a heat exchanger/cooler 220 that cools the air to the desired temperature before exiting entering delivery tube 20. The cooler could be a simple tube immersed in a liquid nitrogen dewar or an electronic Peltier cooling unit Control electronics 230 control the exit air pressure and temperature by controlling the compressor 200 and cooler 220. User input devices such as knobs, or push buttons on the control unit can be used to adjusted the desired pressure and temperature. An optional LCD or other electronic screen on the control unit 10 can provide the user with the current settings and actual readings from sensors on the device 30.

Figure 4:
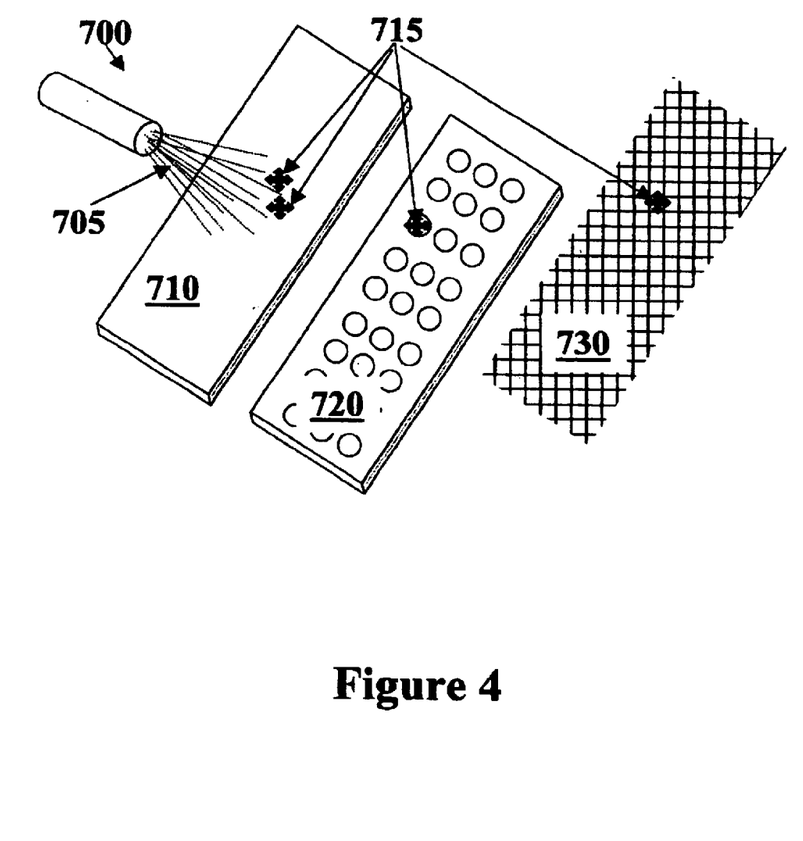

FIG. 4 shows an alternative technique for producing the particles. An atomizing nozzle 700 sprays water mist or droplets 705 at nonperforated sheet, strip, or plane 710 contained within cool container causing ice crystal 715 to form. The atomizer can also mist perforated sheet, strip, or plane 720 causing ice crystal 715 to form. The atomizer can also mist flexible or inflexible sheet, strip, band, or plane of screen-like material 730 causing ice crystal 715 to form. These sheets and strips are preferably made of some metal with high thermal conductivity; however, they can be made from plastics, ceramics glasses or other materials. Various mechanical methods may be used to remove the delicate ice crystals from the structures upon which they have been deposited and include scrapers brushes and acoustic/sonic/shock means.

Figure 5:
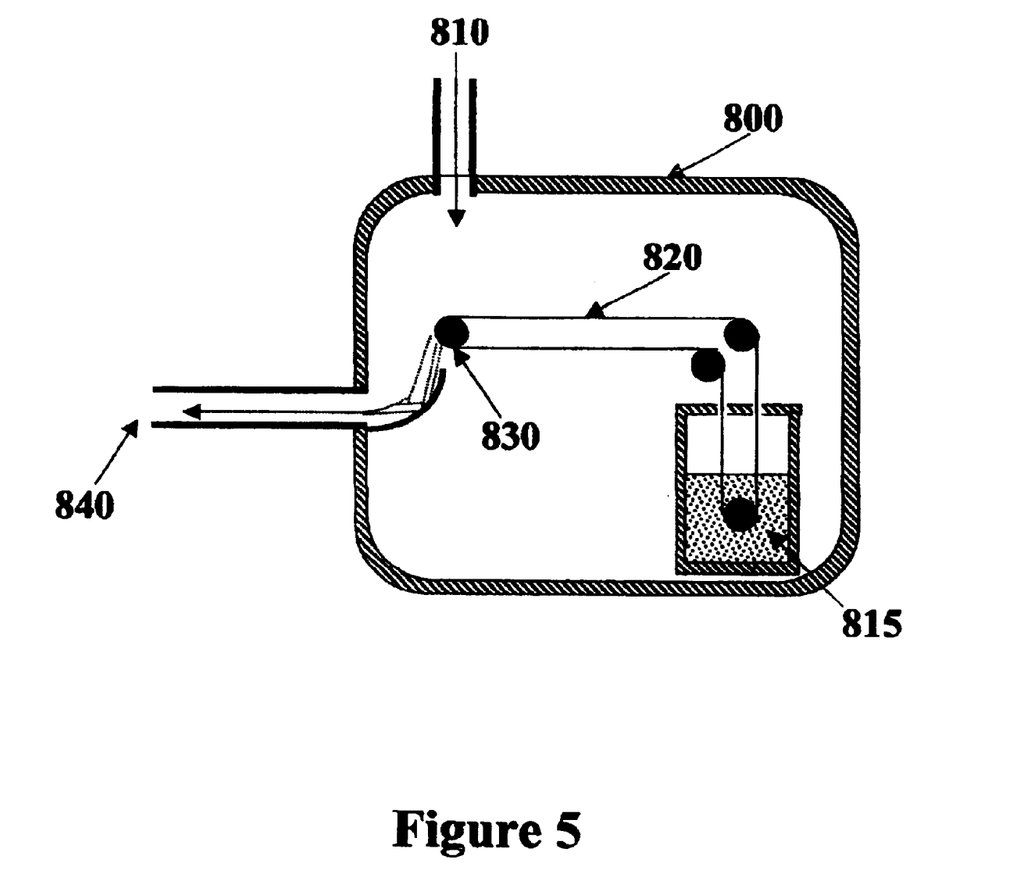

FIG. 5 shows an alternative technique for producing the particles. A vessel 800 is filled with cold carrier fluid through a port 810. A continuous band of a mesh/screen 820 moves through a temperature controlled water bath 815 that coats the mesh with a thin water layer. Once the mesh enters the cold environment, ice crystals form and are brushed/scraped from the mesh at brush 830. The cold carrier fluid exits through port 840 and delivers the ice particles through a tube to the target tissue. Temperature and pressure sensors within the vessel 800 can be used by the control device 10 to adjust carrier fluid temperature and input pressure.

In one embodiment, thermocouples may be placed along the insulated delivery system path, including at the delivery tip (e.g., tube 20 and delivery tip 30 in FIG. 1), to monitor the temperature of the carrier gas and biocompatible particles. The objective is to propel unmelted crystals or cold droplets at the skin; it is not desirable to have either fluid shooting out the tip or excessively cold crystals that can damage the skin. A thermostat or temperature feedback device may be beneficial to control and adjust the temperature of the particles and gas produced in the delivery system and exiting the delivery tip.

The delivery apparatus may also include an attachment to measure the surface temperature of the skin using an infrared sensor or direct thermocouple (See sensor 180 in FIG. 2). Additionally, the delivery apparatus may include pressure sensitive sensors (e.g., spring-loaded) that allow the operator to sense and alter contour by hand-pressure. Such a device can be applied to the delivery tip, so the more pressure the operator applies, the greater the velocity and volume of shooting particles that are delivered to a certain area. Applying differential pressure is advantageous to reduce a tissue mound, lip, or edge with feedback just by operator feel. The pressure-sensitive tip can provide feedback to the carrier gas delivery and particle flow controls to increase the amount of flow and particles to the surface, which will increase the penetration depth. A feedback sensor (e.g., optical) may be used to monitor the penetration depth of particles at the skin surface. One possible optical technique that could be incorporated into the system is optical coherence tomography (OCT or OCDR). This optical technique can image several millimeters into tissue and provide the user with information about how tissue is being removed. The operator may be alerted by a series of audible sounds as to how fast to move the tip for maximum efficiency on a particular patient's skin. Maximum efficiency is based on the skin temperature, particle load and velocity, and type of particle shot at the skin.

Companion and Integral Chemicals

Companion-chemicals and classifications of substances that may be used to comprise a frozen cutaneous projectile delivered by high-pressure cold gas:

Steroids including estrogen, testosterone, flucinonide, betamethasone, hydrocortisone and cortisone derivatives;

Salts including sodium chloride and calcium chloride;

Buffers including sodium bicarbonate and phosphates;

Antifreezes such as polyethylene glycol;

Antipsoriasis drugs such as dovonex, tazarotene, tars, steroids;

Pigmenters/coloring agents including dihydroxyacetone, melanin, hemoglobin or hemosiderin;

Mineral coloring agents including iron and copper;

Depigmenters including hydroquinones, and phenolic compounds;

Tattooing or body artistry including airbrushing with oil and water-soluble skin dyes;

Fat-soluble vitamins including A, D, E, K;

Water-soluble vitamins including B complex and C;

Minerals including iron, selenium, calcium, and magnesium;

Dyes including vegetable: carrots, beets, wildflowers, native American Indian dyes, berries;

Dyes, e.g., fluorescent dyes;

Preservatives including benzoates, parabens and salicylates;

Antioxidants including Coenzyme Q and Vitamin E and salicylic acid;

Anesthetics including xylocaine, bupivicane, carbocane, all amide and ester -based-local-anesthetics (as well as all remaining local and topical anesthetics);

Vasoconstrictors including epinephrine and ephedrine and congeners thereof;

Alpha-hydroxy acids, Beta-hydroxy acids, halogenated acetic acids, other peeling acids;

Irritants including acids, croton oil, and soaps including salts of fatty acids;

Antibiotics, e.g., penicillin, amoxicillin, erythromycin, tetracycline, monocycline, minocycline, mupirocin, flagyl, ciprofloxacin, polymixin, gentamycin and other antibacterials;

Antivirals including acyclovir, famciclovir, valtrex, etc,;

Antifungals including imidazoles, nystatin, and griseofulvin, and sporonox;

Depilatories such as eflornithine hydrochloride;

Co-enzymes;

Proanthrocyanins such as maritime pine extract (Pycnogenol™);

Tocopheryl acetate;

Vitamin A precursors; and

Microparticles (lactic-glycolic acid) and microspheres and liposomes and proteins (such as albumin) with relative stability in ice.

The present invention can propel into the skin any of the materials mentioned in this section, as well as propel into the skin virtually any other medicine known to man. For drugs that are oil-soluble or poorly soluble in water, these compounds can be carried by microparticles (lactic-glycolic acid), microspheres, liposomes and proteins (such as albumin) that have relative stability in ice. These structures may be fabricated biochemically to coat and therefore contain any of the companion and integral chemicals mentioned above and virtually any other medicine known to man. These structures are a bit fat-soluble and are able to penetrate deeply into the skin by being handed from oil-soluble to oil-soluble layer. All of the above can come in premixed plastic cartridges that can be frozen and put into the ice-blasting gun. Or they can be mixed by the doctor/nurse on site, frozen in a mold and placed into the gun without a plastic jacket or sleeve or cartridge.

The foregoing description of preferred embodiments of the invention is presented for purposes of illustration and description and is not intended to be exhaustive or to limit the invention to the precise form disclosed. Many modifications and variations are possible in light of the above teaching.

We claim:

1. A method of treatment, comprising propelling, from a handholdable housing, frozen biocompatible particles with a cold carrier gas directed at a human skin tissue surface, wherein said cold carrier gas has a temperature that is lower than room temperature and at least cold enough to maintain said frozen biocompatible particles in a tissue modifying form.

2. The method of claim 1, wherein said frozen biocompatible particles are suspended in said cold carrier gas.

3. The method of claim 1, wherein said cold carrier gas has a temperature that is at least cold enough to maintain said frozen biocompatible particles in a frozen form.

4. The method of claim 1, wherein said cold carrier gas comprises a compressible fluid.

5. The method of claim 1, further comprising maintaining said frozen biocompatible particles at a temperature above that which will result in unacceptable tissue death.

6. The method of claim 1, wherein the step of propelling frozen biocompatible particles is carried out with sufficient velocity to cause destruction, loosening, or unbinding of tissues to a desired depth.

7. The method of claim 1, wherein said biocompatible materials are non-toxic and harmonious with the human body and thus do not cause foreign body reactions.

8. The method of claim 1, wherein said biocompatible materials comprise materials that do not cause a significant adverse biological host response.

9. The method of claim 1, wherein said biocompatible materials comprise at least one abrasive material.

10. The method of claim 9, wherein said at least one abrasive material is selected from the group consisting of solid carbon dioxide, frozen $H_2O$, an organic material, an organic polymer, a carbohydrate, a protein, a nucleic acid and an inorganic salt.

11. The method of claim 10, wherein said organic material is selected from the group consisting of urea, an amine and an amide.

12. The method of claim 10, wherein said inorganic is selected from the group consisting of sugar, carbohydrate and protein.

13. The method of claim 10, wherein said inorganic salt is selected from the group consisting of a phosphate, a sulfate, a carbonate and a nitrate.

14. The method of claim 10, further comprising propelling added biocompatible particles along with said abrasive materials.

15. The method of claim 14, wherein said added biocompatible particles are selected from the group consisting of a steroid, a salt, a buffer, an antifreeze, an antipsoriasis drug, a pigment/coloring agent, a mineral coloring agent, a depigmenter, a tattooing chemical, a skin dye, a fat-soluble vitamin, a water-soluble vitamin, a mineral, a dye, a preservatives, an antioxidant, an anesthetic, a vasoconstrictor, an acid, an irritant, an antibiotics, an anti-viral drug, an antifungal compound, a depilatory, a co-enzyme, a proanthrocyanin, tocopheryl acetate, a vitamin A precursor, lactic-glycolic acid, and liposomes.

16. The method of claim 15, wherein said steroid is selected from the group consisting of estrogen, testosterone, betamethasone, flucinonide, hydrocortisone and cortisone derivatives, wherein said salt is selected from the group consisting of sodium chloride and calcium chloride, wherein said buffer is selected from the group consisting of sodium bicarbonate and phosphate, wherein said antifreeze comprises polyethylene glycol, wherein said antipsoriasis drug is selected from the group consisting of dovonex, tazarotene, tar and, a steroid, wherein said pigment/coloring agent is selected from the group consisting of dihydroxyacetone, melanin, hemoglobin and hemosiderin, wherein said mineral coloring agent is selected from the group consisting of iron and copper, wherein said depigmenters is selected from the group consisting of a hydroquinone and a phenolic compound, wherein said tattooing chemical is selected from the group consisting of oil and water-soluble skin dye, wherein said fat-soluble vitamin is a vitamin selected from the group consisting of A, D, E and K, wherein said water-soluble vitamin is a vitamin selected from the group consisting of B complex and C, wherein said mineral is selected from the group consisting of iron, selenium, calcium and magnesium, wherein said dye is a dye selected from the group consisting of a vegetable dye, a berry dye and a fluorescent dye, wherein said preservative is selected from the group consisting of a benzoate, a paraben and a salicylate, wherein said antioxidant is selected from the group consisting of Coenzyme Q, Vitamin E and salicylic acid, wherein said anesthetic is selected from the group consisting of xylocaine, bupivicane, carbocane, local anesthetic and topical anesthetic, wherein said vasoconstrictor is selected from the group consisting of epinephrine and ephedrine and congeners thereof, wherein said acid is selected from the group consisting of alpha-hydroxy acid, beta-hydroxy acid, halogenated acetic acids and other peeling acid, wherein said irritant is selected from the group consisting of acids, croton oil and soaps, wherein said antibiotic is selected from the group consisting of penicillin, amoxicillin, erythromycin, tetracycline, monocycline, minocycline, mupirocin, flagyl, ciprofloxacin, polymixin, gentamycin and an antibacterial, wherein said antiviral is selected from the group consisting of acyclovir, famciclovir and valtrex, wherein said antifungals is selected from the group consisting of imidazoles, nystatin, griseofulvin, and sporonox, wherein said depilatory comprises eflornithine hydrochloride and wherein said proanthrocyanin comprises maritime pine extract.

17. The method of claim 1, wherein said cold carrier gas comprises dehumidified air.

18. The method of claim 1, wherein said cold carrier gas comprises an inert gas.

19. The method of claim 18, wherein said inert gas is selected from the group consisting of nitrogen, helium and argon.

20. The method of claim 1, further comprising controlling the temperature of said cold carrier gas.

21. The method of claim 1, further comprising controlling the pressure of said cold carrier gas.

22. The method of claims 1, further comprising controlling the particle density of said frozen biocompatible particles.

23. The method of claim 1, further comprising monitoring the temperature of said tissue surface.

24. The method of claim 23, further comprising automatically turning off the flow of said frozen biocompatible particles if the temperature of said tissue surface drops below a preset limit.

25. The method of claim 1, further comprising monitoring the velocity of said frozen biocompatible particles into the surface of said tissue.

26. The met hod of claim 1, wherein said frozen biocompatible particles are selected from the group consisting of solid carbon dioxide, frozen $H_2O$, organic material, organic polymer, carbohydrate, protein, inorganic salt, a nucleic acid, a steroid, a salt, a buffer, an antifreeze, an antipsoriasis drug, a pigmenter/coloring agent, a mineral coloring agent, a depigmenter, a tattooing chemical, a skin dye, a fat-soluble vitamin, a water-soluble vitamin, a mineral, a dye, a preservatives, an antioxidant, an anesthetic, a vasoconstrictor, an acid, an irritant, an antibiotics, an antiviral drug, an antifungal compound, a depilatory, a co-enzyme, a proanthrocyanins, tocopheryl acetate, a vitamin A precursor, lactic-glycolic acid, and liposomes.

27. The method of claim 26, wherein said steroid is selected from the group consisting of betamethasone, estrogen, testosterone, flucinonide, hydrocortisone and cortisone derivatives, wherein said salt is selected from the group consisting of sodium chloride and calcium chloride, wherein said buffer is selected from the group consisting of sodium bicarbonate and phosphate, wherein said antifreeze comprises polyethylene glycol, wherein said antipsoriasis drug is selected from the group consisting of dovonex, tazarotene, tar and, a steroid, wherein said pigmenters/coloring agent is selected from the group consisting of dihydroxyacetone, melanin, hemoglobin and hemosiderin, wherein said mineral coloring agent is selected from the group consisting of iron and copper, wherein said depigmenters is selected from the group consisting of a hydroquinone and a phenolic compound, wherein said tattooing chemical is selected from the group consisting of oil and water-soluble skin dye, wherein said fat-soluble vitamin is a vitamin selected from the group consisting of A, D, E and K, wherein said water-soluble vitamin is a vitamin selected from the group consisting of B complex and C, wherein said mineral is selected from the group consisting of iron, selenium, calcium and magnesium, wherein said dye is a dye selected from the group consisting of a vegetable dye, a berry dye and a fluorescent dye, wherein said preservative is selected from the group consisting of a benzoate, a paraben and a salicylate, wherein said antioxidant is selected from the group consisting of Coenzyme Q, Vitamin E and salicylic acid, wherein said anesthetic is selected from the group consisting of xylocaine, bupivicane, carbocane, local anesthetic and topical anesthetic, wherein said vasoconstrictors is selected from the group consisting of epinephrine and ephedrine and congeners thereo, wherein said acid is selected from the group consisting of alpha-hydroxy acid, beta-hydroxy acid, halogenated acetic acids and other peeling acid, wherein said irritant is selected from the group consisting of acids, croton oil and soaps, wherein said antibiotic is selected from the group consisting of penicillin, amoxicillin, erythromycin, tetracycline, monocycline, minocycline, mupirocin, flagyl, ciprofloxacin, polymixin, gentamycin and an antibacterial, wherein said antiviral is selected from the group consisting of acyclovir, famciclovir and valtrex, wherein said antifungals is selected from the group consisting of imidazoles, nystatin, griseofulvin, and sporonox, wherein said depilatory comprises eflornithine hydrochloride and wherein said proanthrocyanin comprises maritime pine extract.

28. The treatment apparatus of claim 1, further comprising removing excess materials or reaction by-products that build up on the surface of said tissue.

29. A treatment apparatus, comprising:
means for forming frozen biocompatible particles; and
means for propelling said frozen biocompatible particles with a cold carrier gas at a skin tissue surface, wherein said means for propelling comprises a handholdable housing, wherein said cold carrier gas has a temperature that is lower than room temperature and at least cold enough to maintain said frozen biocompatible particles in a tissue modifying form.

30. The treatment apparatus of claim 29, wherein said means for forming frozen biocompatible particles comprises:
a mechanism for holding an integral unit of frozen biocompatible material;
a cutting mechanism for separating biocompatible particles from said integral unit of frozen biocompatible material; and
means for delivering said integral unit of frozen biocompatible material into said cutting mechanism.

31. The treatment apparatus of claim 30, wherein said mechanism for holding an integral unit of biocompatible material comprises packing material.

32. The treatment apparatus of claim 31, wherein said packing material has a low thermal conductivity.

33. The treatment apparatus of claim 30, wherein said cutting mechanism is selected from the group consisting of a rotating grinder wheel, a wire brush, a sharp cutting edge and a rasp.

34. The apparatus of claim 30, wherein said cutting mechanism is driven by a motor selected from the group consisting of an electric motor and a pneumatically driven motor.

35. The treatment apparatus of claim 34, wherein said motor comprises a variable speed control to adjust the particle density of said frozen biocompatible particles.

36. The treatment apparatus of claim 30, wherein said means for delivering said integral unit of frozen biocompatible material into said cutting mechanism comprises a piston.

37. The treatment apparatus of claim 36, wherein said piston is driven by means selected from the group consisting of an electric motor and a pneumatically driven actuator.

38. The treatment apparatus of claim 29, wherein said means for forming frozen biocompatible particles comprises an atomizing nozzle that sprays a water mist or droplets at an ice forming element contained within a cool container causing ice crystal to form.

39. The treatment apparatus of claim 38, wherein said ice forming element is selected from the group consisting of a sheet of material, a strip of material, a band of material and a plane of material.

40. The treatment apparatus of claim 39, further comprising means for removing ice crystals from said ice forming element.

41. The treatment apparatus of claim 40, wherein said means for removing ice crystals from said ice forming element is selected from the group consisting of a scraper, a brush, means for producing at least one acoustic waves, means for producing at least one sonic wave and means for producing at least one shock wave.

42. The treatment apparatus of claim 29, wherein said means for forming frozen biocompatible particles comprises:

a vessel through which said cold carrier gas flows;

a temperature controlled water repository;

a continuous perforated band;

means for moving said continuous perforated band through said temperature controlled water repository and said vessel, wherein said water repository coats said continuous perforated band with a thin water layer, wherein ice crystals form on said continuous perforated band when it enters the cold environment of said vessel; and means for removing said ice crystals from said continuous perforated band, wherein said cold carrier gas picks up said ice crystals and delivers them to said tissue.

43. The treatment apparatus of claim 29, wherein said means for propelling said frozen biocompatible particles comprises a control unit connected to a handheld device by a delivery tube and a signal cable.

44. The treatment apparatus of claim 43, wherein said control unit comprises a cooler to cool said carrier gas, wherein said control unit further comprises a compressor to force said carrier gas through said delivery tube to said handheld device for delivery to said tissue surface.

45. The treatment apparatus of claim 43, wherein said control unit comprises means for adjusting the temperature of said carrier gas.

46. The treatment apparatus of claim 43, wherein said control unit comprises means for adjusting the pressure of said carrier gas.

47. The treatment apparatus of claim 43, further comprising a vacuum tube that removes excess materials or reaction byproducts that build up on the surface of said tissue.

48. The treatment apparatus of claim 43, wherein said means for forming said frozen biocompatible particles are located within said handheld device, wherein said handheld device comprises:

a handholdable housing;

an entrance port to allow entry of said cold carrier gas into said handheld device; and an exit port to allow egress of said carrier gas along with said frozen biocompatible particles.

49. The treatment apparatus of claim 48, wherein said handholdable housing comprises insulation to protect the user.

50. The treatment apparatus of claim 48, further comprising an electric heater integrated into the outside wall of said handholdable housing to improve user comfort.

51. The treatment apparatus of claim 48, wherein said exit port comprises an aperture selected from the group consisting of a slit, a rectangle, a square, a circle and an ellipse.

52. The treatment apparatus of claim 48, wherein said handholdable housing comprises a light source to send a beam of light to illuminate said frozen biocompatible particles as they are propelled onto said tissue, wherein the light scattered by the particles can be seen by the user and provides confirmation that particles are flowing.

53. The treatment apparatus of claim 48, wherein said handholdable housing comprises a light source to send a beam of light to illuminate said frozen biocompatible particles as they are propelled onto said tissue and an optical detector that measures the light scattered by the particles.

54. The treatment apparatus of claim 48, further comprising a pressure sensitive sensor located on said handholdable housing, wherein said pressure sensitive sensor allows the operator to sense and alter the pressure delivered according to the amount of hand-pressure exerted, wherein the more pressure the operator applies, the greater the velocity and volume of shooting particles that are delivered to a certain area.

* * * * *